United States Patent [19]
Meibauer

[11] Patent Number: 5,904,153
[45] Date of Patent: May 18, 1999

[54] DISPOSABLE DENTAL FLOSSING DEVICE

[76] Inventor: Robert H. Meibauer, P.O. Box 3116, Sea Bright, N.J. 07760

[21] Appl. No.: 09/055,137

[22] Filed: Apr. 3, 1998

[51] Int. Cl.⁶ .................................................. A61C 15/00
[52] U.S. Cl. ........................... 132/329; 132/322; 132/323
[58] Field of Search ..................... 132/329, 321, 132/322, 323, 324, 325, 326; 433/82, 125, 118, 127, 147, 166, 216; 15/167.1, 250.17, 22.1, 22.2, 143.1

[56] References Cited

U.S. PATENT DOCUMENTS

| | | | |
|---|---|---|---|
| 3,631,597 | 1/1972 | Lieb et al. | 433/216 |
| 3,927,436 | 12/1975 | Inoue et al. | 15/250.17 |
| 5,000,684 | 3/1991 | Odrich | 433/125 |
| 5,177,826 | 1/1993 | Vrignaud et al. | 15/22.1 |
| 5,186,627 | 2/1993 | Amit et al. | 433/216 |
| 5,253,382 | 10/1993 | Beny | 15/22.1 |
| 5,261,430 | 11/1993 | Mochel | 132/322 |
| 5,700,146 | 12/1997 | Kucar | 433/82 |
| 5,749,381 | 5/1998 | Butler et al. | 132/309 |

*Primary Examiner*—Gene Mancene
*Assistant Examiner*—Pedro Philo Gene
*Attorney, Agent, or Firm*—Mandel and Peslak; Arthur M. Peslak

[57] ABSTRACT

A disposable flossing device is disclosed. The disposable flossing device is adapted for use with the conventional dental handpiece or any other device providing rotary input motion. The disposable flossing device converts the rotary input motion to reciprocating linear motion so that the dental floss will reciprocate through a linear plane. In addition to flossing, other attachments to the conventional dental handpiece such as brushes and polishers can also be operated with the linear motion of the disclosed device.

4 Claims, 6 Drawing Sheets

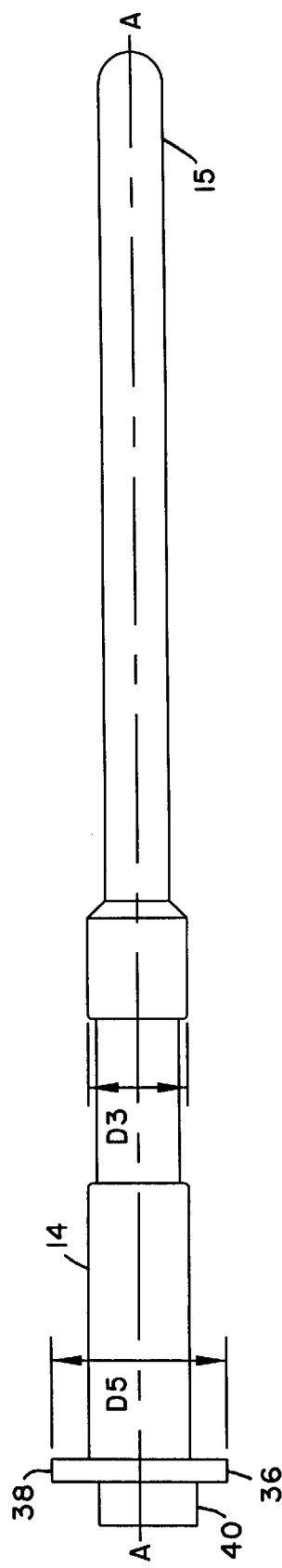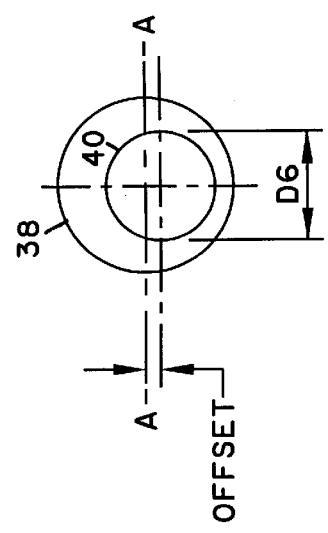
FIG. 4A
FIG. 4B

DISPOSABLE DENTAL FLOSSING DEVICE

The present invention relates to a device for tooth flossing that attaches to a conventional dental handpiece or a power driven hand held flossing device. The present invention is directed to producing true linear reciprocation of the dental floss in a plane parallel to the dentition surface between the teeth.

BACKGROUND OF THE INVENTION

It is well known in the field of dentistry that failure to remove plaque from dentition surfaces and debris between dentitions is a principal cause of dental diseases such as tooth decay and gingivitis for example. Removal of plaque and debris by brushing is the commonest and easiest method known. However, brushing is generally inadequate especially when self-administered. A more efficient and known technique is the cleaning of dentition surfaces and areas between such surfaces by using a dental tape or floss (hereinafter generally termed "floss") which is moved reciprocally over and between the dentition surfaces. Furthermore, the reciprocating motion of the floss as it is manipulated over and between the dentition surfaces is beneficial as a treatment for and prevention of periodontal diseases, such as gingivitis and the like. This beneficial result occurs since the free margin of the gingivi which is adjacent to the individual teeth of the dentition and forms the gingival sulcus can be readily reached by dental floss, although it is generally inaccessible to a brush or other instruments, and the sulci are subject to the invasion of plaque or colonies of bacteria which cause diseases of these tissues. Thus, floss, in general, is particularly beneficial in removing plaque and debris, as well as serving as a vehicle for the application of medication. On the other hand, dental tape or floss is inconvenient and awkward to handle.

Consequently, much development has been undertaken in the past to provide dental tape or floss in various forms which is more convenient to handle and use. In addition, much development has taken place to provide mechanical devices for the flossing of dentition surfaces. Therefore, past developments have broadly involved provision of dental tape or floss in various forms to render the same easier to use and the provision of mechanical devices to support or hold the dental tape or floss in a manner to that it can be employed with greater efficiency and facility.

As an example of such developments, U.S. Pat. No. 4,172,687 discloses a flossing device which is manipulated by hand and provided with a pair of spaced, resilient arms having fingers extending therefrom. The fingers are equipped with knobs on their distal ends and a length of dental tape or floss having a grommet on each end is disposed over the knobs on the ends of the fingers. A somewhat similar device, but which is power driven, is disclosed in U.S. Pat. No. 4,014,354. The disclosure in this latter patent indicates that the dental tape or floss is tensioned between a pair of L-shaped arms attached to a handle which is adapted to be driven by the power element. On the other hand, U.S. Pat. No. 3,927,686 discloses a hand manipulated flossing device which includes a handle and an adjustable head provided with a single strand or a plurality of strands of dental tape of floss.

Still another dentition surface cleaning device is disclosed in U.S. Pat. No. 3,835,872 in which a flexible dental tape or floss disposed on a handle having a detachable yoke for tautly supporting a run of the tape, the tape being attached to a pair of anchor pins disposed on the handle and one of which is disposed on a reciprocable trigger mounted in the handle for the purpose of tensioning the tape. The tape per se is provided with non-elastic loops at each end which are disposed over the previously mentioned pins. U.S. Pat. No. 3,828,804 discloses still another apparatus which is a hand manipulated device for cleaning teeth that includes a handle with a nub disposed thereon and which is provided with extending, spaced arms having notches at the ends thereof. An endless or circular elastomeric dental floss or tape is disposed in the notches thereby passing across the space between the arms and around the nub. In a variation of the device, a simple length of elastomeric band is anchored in the notches of the arms by means of shim or heads.

A further dentition cleaning instrument is disclosed in U.S. Pat. No. 3,759,274 in which a strand of dental floss is mounted on an extended fork which supports the strand and permits an oscillating movement which is imparted thereto by a drive means. In addition, the device also includes a spool for carrying the strand for use in each subsequent cleaning cycle. A still further dentition cleaning device is disclosed in U.S. Pat. No. 3,667,483 in which the device includes a pair of projecting arms disposed on a support frame, the arms being provided with guides at their outer ends to receive and permit relative movement of floss which passes from a spool to a take-up reel mounted on the supporting frame. The floss is driven in a reciprocating manner through a device provided with means to alternately remove floss from the supply spool and feed it to the takeup spool after each use.

In U.S. Pat. No. 3,552,022 there is disclosed another powered dentition cleaning or polishing device. This patent discloses a tool having a conical stem portion which is adapted to be inserted in and removed from a handle in which a reciprocating socket is provided therefore. The operating end of the tool is wedgelike and pointed, two broad sides being rough in order to abrade dentition surfaces and a third side thereof being narrow and smooth in order to prevent injury to the gingiva. Another power cleaning device is disclosed in U.S. Pat. No. 3,534,745. This device includes a housing provided with spaced prongs and a dental tape or floss holder and supply unit adapted to be removeably attached to a power unit which imparts reciprocating motion to the tape as well as permitting the feeding of new tape to the unit after each use. Finally, U.S. Pat. No. 3,421,524 discloses a power driven dentition cleaning device including a power unit which is adapted to receive a cleaning unit which includes an elongated shaft provided with a pair of spaced tines. A dental tape or floss supply holding member is removeably positioned on the power unit and the dental tape or floss is fed therefrom through an eyelet in each of the tines and back to the supply holding member where it is taken up on a take-up spool.

Mention may also be made of U.S. Pat. No. 4,307,740, U.S. Pat. No. 4,830,032, and U.S. Pat. No. 5,069,233, all of which involve devices in which the floss is held in fixed position relative to the structure which supports it, and that structure, along with the floss, is power driven.

While the various devices disclosed in the above-mentioned patents are useful for cleaning dentition surfaces, they still exhibit various disadvantages. For example, many of them are extremely complex in structure and consequently relatively expensive to manufacture. In addition, many of the known structures are relatively difficult to employ, often being difficult to load and requiring complex adjustment to impart the required tautness to the dental tape or floss utilized therewith.

In addition, many of the known devices do not provide maximum contact of the floss with the dentition surfaces to be cleaned and, in addition, due to their construction, necessitate the use of more than the needed amount of dental tape or floss for carrying out a given cleaning operation.

The disadvantages of the above-described devices have been substantially eliminated by the devices and processes set forth in my prior patents, U.S. Pat. No. 4,339,957 and U.S. Pat. No. 5,400,811. In Pat. No. 4,339,957, there is disclosed a dental prophylaxis device which comprises in combination a housing means provided with an axial cavity and having a pair of spaced tines provided with slotted openings disposed thereon and projecting outwardly therefrom, stationary support means on the housing in the vicinity of the base of each of the tines and oscillating support means located on the housing between the bases of the tines and which is supported on a cylindrical sleeve that is disposed axially within the cavity of the housing, the housing means being adapted to be connected to driving means to drive the oscillating support means through the cylindrical sleeve.

The dental prophylaxis process disclosed in U.S. Pat. No. 4,338,957 comprises contacting the dentition surfaces to be treated with a dental floss having a thread segment which is provided with a non-elastic loop at one end and an elastic loop at the opposite end, reciprocating the thread segment over the surfaces of the dentition to be treated, while expanding and contracting the elastic loop in response to the application of tensile force to the dental floss as it reciprocates over the dentition surfaces and absorbing the tensile forces which is imparted to the dental floss when it encounters resistance as it reciprocates over the dentition surfaces and the elastic loop expands.

The device disclosed in my U.S. Pat. No. 5,400,811 comprises a housing, a pair of stationary tines extending therefrom adapted to receive and support a length of dental floss extending therebetween, said length of floss having a pair of free ends extending therefrom beyond said tines, an exposed oscillatable part mounted on said housing, means on said part for receiving said pair of free floss ends, and drive means in said housing operatively connected to said part for driving it in oscillation, whereby, when said part is driven in oscillation, said floss translates back and forth between said tines.

While my previous devices and process have substantially eliminated the disadvantage of prior devices, there still exists a need for further improvement. The present invention fulfills this need.

All of the prior flossing devices suffered from the deficiency that when activated the floss does not reciprocate in a linear plane. Rather, the movement of the floss in these prior flossing devices entailed reciprocation through an arc. Thus, the floss in contact with the dentition surface was in reality only the point at the bottom of the arc. It is thus an object of the present invention to provide a flossing device whereby the floss will reciprocate in a linear plane thus ensuring that a longer section of floss will contact the dentition surface during reciprocation. It is a further object of the present invention to simplify the prior flossing devices and provide a device that is disposable and can be readily adapted to the conventional dental handpiece.

SUMMARY OF THE INVENTION

The present invention is directed to a disposable flossing device that fits on the distal end of the conventional dental handpiece used by dental professionals. The disposable flossing device of the present invention converts the rotary motion of the drive shaft on the conventional dental handpiece into true linear motion of the floss in a horizontal plane rather than the arc that is produced in prior flossing devices. Although the disposable flossing device in the preferred embodiment is specifically adapted to the conventional dental handpiece, those of ordinary skill in the art will readily recognize that it can be adapted to any power-driven rotating shaft device.

The present invention is thus directed to a disposable flossing device adapted to be driven by a first shaft providing rotary input motion to the disposable flossing device and comprising: a hollow body comprising a distal end and a proximal end and adapted on its proximal end for connection to a device containing the first shaft providing rotary input motion; a second shaft comprising a distal end and a proximal end slidingly mounted in the hollow body and connected on its proximal end to the first shaft which thereby provides rotary input motion to the second shaft and further comprising means on its distal end for converting the rotary input motion to linear reciprocating motion at the distal end of the second shaft; and flossing means mounted to the distal end of the hollow body and driven by the distal end of the second shaft whereby the means on the distal end of the second shaft drives the flossing means in such a manner that the flossing means reciprocates in a linear plane.

BRIEF DESCRIPTION OF THE DRAWINGS

FIGS. 4A and 4B are plan views of a shaft used in connection with the disposable flossing device.

DETAILED DESCRIPTION OF THE INVENTION

Figure 1:
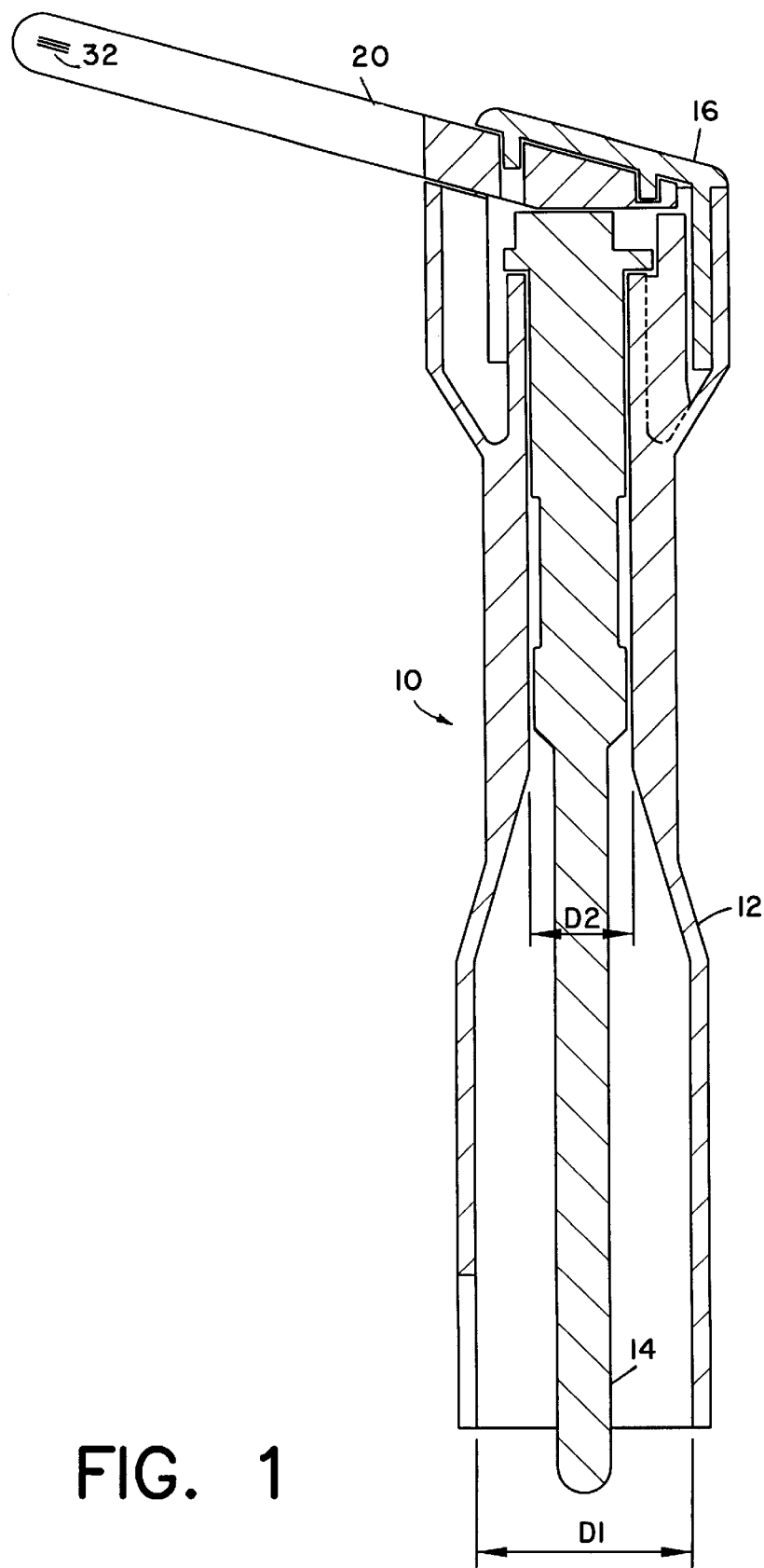
FIG. 1 is a cross-sectional view of the disposable flossing device of the present invention.
Figure 2:
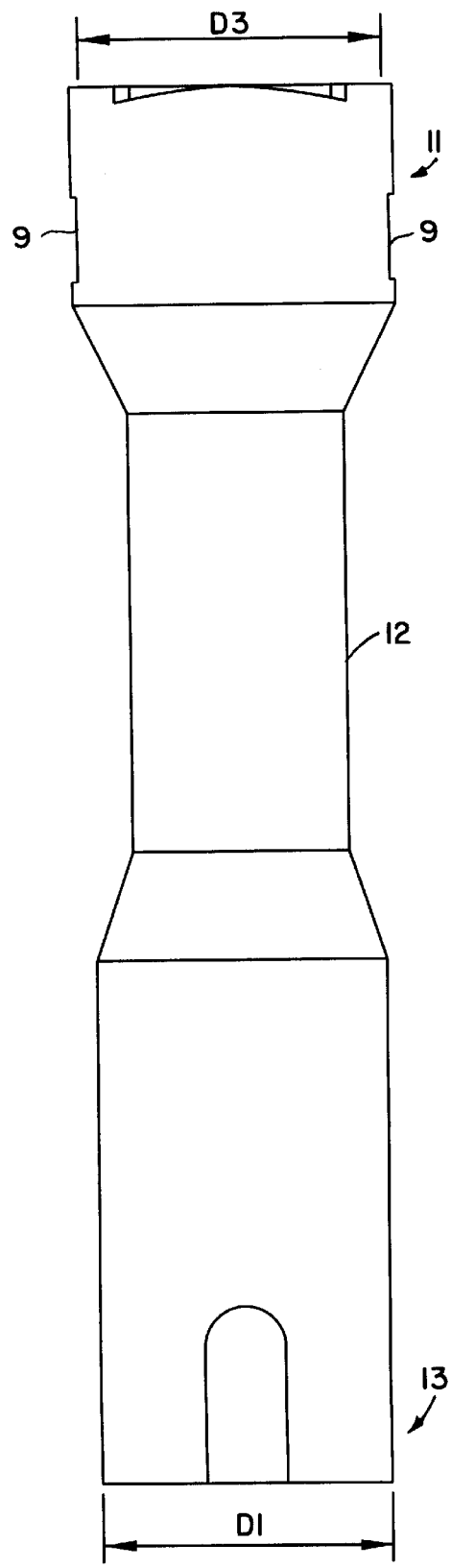
FIG. 2 is a plan view of the body of the disposable flossing device.

The present invention is directed to a disposable flossing device 10 as illustrated in the figures. As shown in FIG. 1 and 2, the flossing device 10 comprises a cylindrical hollow body 12 of varying cross-sectional diameter with a distal end 11 and a proximal end 13. The inside diameter D1 of the proximal end 13 of hollow body 12 is adapted, in this embodiment, to be slidingly received over the distal end of a conventional dental handpiece and secured thereto. Those of ordinary skill in the art are fully familiar with such dental handpieces and the conventional methods of attaching parts thereto.

As shown in FIG. 1, the inside diameter D2 of the center portion of hollow body 12 is adapted to slidingly receive shaft 14. Shaft 14 is illustrated in more detail in FIGS. 4A and 4B. Shaft 14 comprises an axis A'A, a distal end 36, a proximal end 15, and is of varying cross-sectional diameter. Shaft 14 is adapted to be driven on its proximal end 15 by the rotary motion imparted by the drive shaft of a conventional dental handpiece. The diameter D3 of shaft 14 and inside diameter D2 of the center portion of hollow body 12 are sized to allow rotation of shaft 14 within hollow body 12.

Figure 5B:
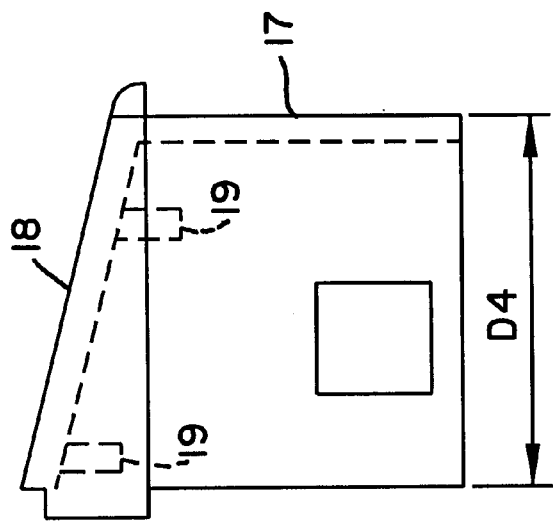
FIG. 5A and 5B are plan views of a cap used in connection with the disposable flossing device.
Figure 5A:
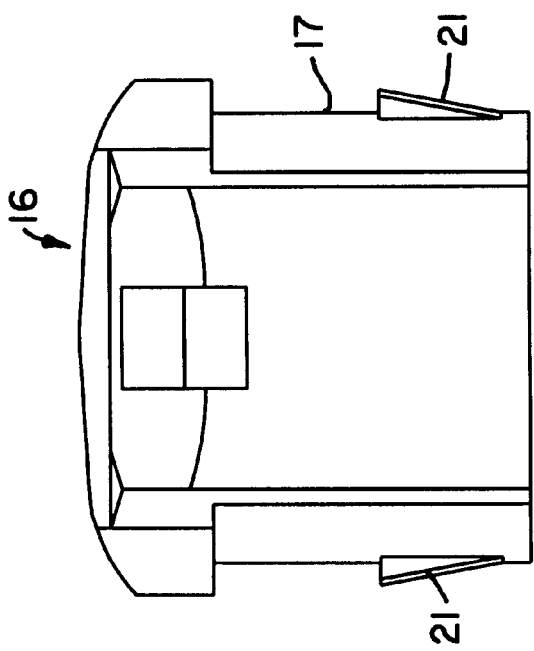
Figure 6A:
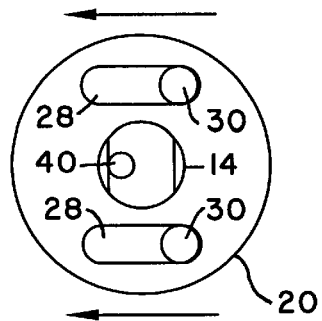
FIG. 6A, 6B, 6C, and 6D are sectional views illustrating the use of the disposable flossing device.
Figure 6B:
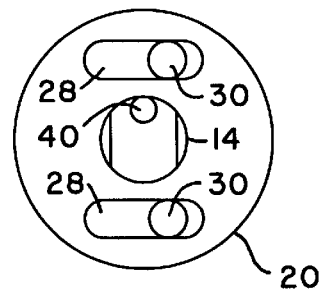
Figure 6C:
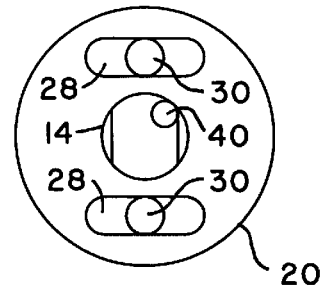
Figure 6D:
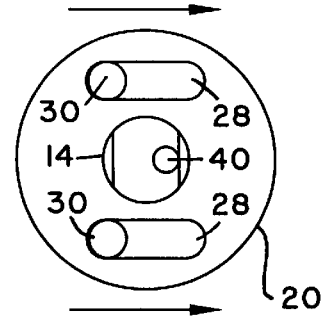

As shown in FIGS. 1 and 2, the inside diameter D3 of the distal end 11 of hollow body 12 is adapted to slidingly receive cap 16. The distal end 11 of hollow body 12 also contains two approximately rectangular cut-outs 9 spaced 180 degrees apart on the exterior of hollow body 12. Cap 16 is illustrated in more detail in FIGS. 5A and 5B. Cap 16 comprises a cylindrical bottom portion 17 of outside diameter D4. The outer surface of cylindrical bottom portion 17 also comprises two approximately rectangular projections 21 spaced 180 degrees apart. Outside diameter D4 and diameter D3 are sized so that cap 16 is slidingly received in the distal end 11 of hollow body 12. The position of cap 16 prior to insertion should be such that the projections 21 are aligned with the cut-outs 9 in hollow body 12. Thus, when cap 16 is slidingly received in the distal end 11 of hollow body 12, the projections 21 protrude through the cut-outs 9 and thereby lock cap 16 into place.

Figure 3:
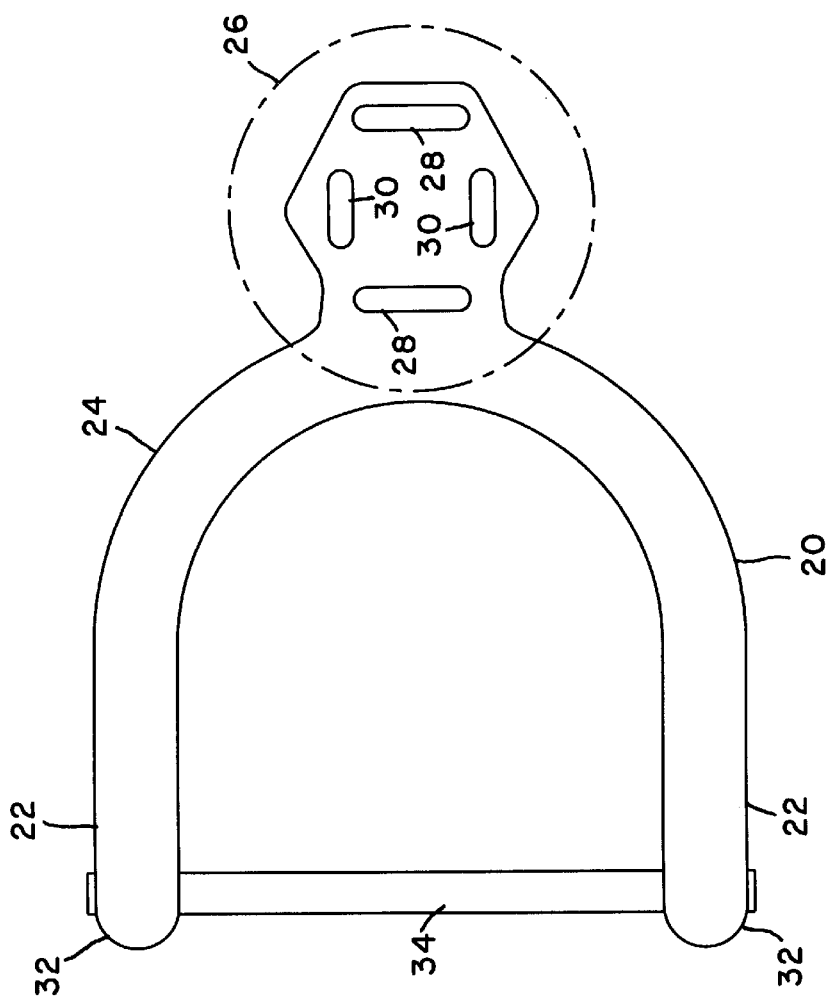
FIG. 3 is a plan view of a fork used in connection with the disposable flossing device.

Cap 16 further comprises a hollow top portion 18 integral with bottom cylindrical portion 17. Mounted on the interior surface of top portion 18 are two projections 19. Hollow top portion 18 of cap 16 is adapted to receive fork 20. Fork 20 is illustrated in more detail in FIG. 3. Fork 20 comprises a pair of tines 22 on its distal end that are integral with a semicircular base portion 24 on its proximal end. Integral with semicircular base portion 24 is tab 26. Tabs 26 comprise slots 28 and projecting ribs 30. Slots 28 are adapted to receive the projections 19 on the interior surface of top portion 18 of cap 16.

The tines 22 are each provided with a slot 32. A small piece of dental tape or floss 34 will be cemented into each of the slots 32. In that way, the dental tape or floss 34 will span the space between tines 22. The dental tape or floss 34 will be mounted in the holes in such a manner to give the proper tension for cleaning the dentition surfaces in operation.

The distal end 36 of the shaft 14 is shown in further detail in FIG. 4B. The shaft 14 is provided with a flange 38 of diameter D5 axially aligned with the axis A—A of shaft 14. The extreme distal portion of the shaft 14 is of diameter D6, is offset from axis A—A as shown in FIG. 4B and forms a cam 40.

In use shaft 14 will drive fork 20 in a linear reciprocating motion as described below. As shown in FIG. 6-A, the cam 40 will contact the projecting ribs 30 which will cause the fork 20 to slide in the slots 28 toward the left in FIG. 6-A. As shown in FIGS. 6-B and 6-C, the cam 40 has rotated in FIG. 6-B about 90 degrees and in FIG. 6-C about 135 degrees respectively from the position shown in FIG. 6-A. In neither case is the cam 40 in contact with the projecting ribs 30 on fork 20. As shown in FIG. 6-D, the cam 40 has rotated 180 degrees from the position shown in FIG. 6-A. In FIG. 6-D, the cam 40 is again in contact with fork 20 and pushes the fork 20 toward the right in FIG. 6-D. The cam 40 then rotates 180 degrees again back to the position shown in FIG. 6-A and the process of pushing the fork 20 from left to right begins again. Thus, the device of the present invention converts the rotary motion imposed on shaft 14 by the conventional dental handpiece into true linear reciprocating motion of the fork 20 and floss 34 in a plane.

In use, the disposable flossing device 10 is placed on the end of a conventional dental handpiece. The shaft 14 is inserted into the end of a rotating shaft in the conventional dental handpiece. The flossing device 10 will be used to clean the dentition surfaces between the patient's teeth. After the patient is treated with the disposable flossing device 10, the device 10 is removed from the dental handpiece and discarded.

Those of ordinary skill in the art will recognize that the embodiments just described merely illustrate the principles of the present invention. For example, the described embodiment could be modified for use with brushes or polishers that also could benefit from the use of linear reciprocating motion. Many modifications may be made thereto without departing from the spirit and scope of the invention as set forth in the following claims.

What is claimed is:

1. A disposable flossing device adapted to be driven by a first shaft providing rotary input motion to the disposable flossing device comprising:

a) a hollow body comprising a distal end and a proximal end and adapted on its proximal end to be slidingly received over a distal end of a device containing the first shaft providing rotary input motion;

b) a second shaft comprising a distal end and a proximal end slidingly mounted in the hollow body and the second shaft connected on the proximal end to the first shaft which thereby provides rotary input motion to the second shaft and further comprising means on the distal end of the second shaft for converting the rotary input motion to linear reciprocating motion at the distal end of the second shaft; and c) flossing means mounted to the distal end of the hollow body and driven by the distal end of the second shaft whereby the means on the distal end of the second shaft drives the flossing means in such a manner that the flossing means reciprocates in a linear plane.

2. The disposable flossing device of claim 1 wherein the device containing the first shaft is a conventional dental handpiece comprising a distal end and a proximal end and whereby the disposable flossing device is slidingly received over the distal end of the conventional dental handpiece.

3. The disposable flossing device of claim 2 wherein the means on the distal end of the second shaft for converting the rotary input motion to linear reciprocating motion comprises a cam that, in use, rotates and contacts the flossing means twice per revolution.

4. The disposable flossing device of claim 3 wherein the flossing means comprises a fork comprising a distal end and a proximal end wherein the distal end comprises two tines, a cap adapted to receive the distal end of the fork and wherein the cap is further adapted to be received in the distal end of the hollow body, a length of dental floss mounted between the tines on the distal end of the fork, and a plurality of projecting ribs on the proximal end of the fork that in use will contact the cam and thereby drive the dental floss in the linear reciprocating motion.

* * * * *